(12) United States Patent  
Schneidt

(10) Patent No.: US 6,174,322 B1  
(45) Date of Patent: Jan. 16, 2001

(54) OCCLUSION DEVICE FOR THE CLOSURE OF A PHYSICAL ANOMALY SUCH AS A VASCULAR APERTURE OR AN APERTURE IN A SEPTUM

(75) Inventor: Bernhard Schneidt, Gelnhausen (DE)

(73) Assignee: Cardia, Inc., Burnsville, MN (US)

( * ) Notice: Under 35 U.S.C. 154(b), the term of this patent shall be extended for 0 days.

(21) Appl. No.: 09/308,203

(22) PCT Filed: Jul. 31, 1998

(86) PCT No.: PCT/US98/15961

§ 371 Date: May 13, 1999

§ 102(e) Date: May 13, 1999

(87) PCT Pub. No.: WO99/07289

PCT Pub. Date: Feb. 18, 1999

(30) Foreign Application Priority Data

Aug. 8, 1997 (DE) .......................................... 297 14 242 U

(51) Int. Cl.[7] ...................................................... A61B 17/08

(52) U.S. Cl. ................................................................ 606/213

(58) Field of Search ................................... 606/213, 151, 606/215, 216, 232, 220; 623/12

(56) References Cited

U.S. PATENT DOCUMENTS

| 5,451,235 | 9/1995 | Lock et al. | 606/213 |
|---|---|---|---|
| 5,725,552 | 3/1998 | Kotula et al. | 606/213 |
| 5,741,297 | 4/1998 | Simon | 606/213 |
| 5,904,703 | * 5/1999 | Gilson | 606/213 |

* cited by examiner

Primary Examiner—Michael H. Thaler  
Assistant Examiner—(Vikki) Hoa B. Trinh  
(74) Attorney, Agent, or Firm—Kinney & Lange, P.A.

(57) ABSTRACT

An occlusion device (10) for the closure of a physical anomaly such as a vascular aperture or an aperture in a septum, includes a center strut (12) with a pair of collapsible support frames (16, 18). Polyvinyl alcohol foam sheets (42, 44) are attached to each of the support frames (16, 18).

25 Claims, 5 Drawing Sheets

OCCLUSION DEVICE FOR THE CLOSURE OF A PHYSICAL ANOMALY SUCH AS A VASCULAR APERTURE OR AN APERTURE IN A SEPTUM

BACKGROUND OF THE INVENTION

The invention relates to an occlusion device for the closure of a physical anomaly such as a vascular aperture or an aperture in a septum, such as patent ductus arteriosus, atrial septal defect, patent foramen ovale, or ventricular septal defect comprising an occluding body extending at least within the aperture with a center piece extending in the axial direction of said occluding body as well as wire-like, elastic fixation devices emanating from the occluding body or its center piece, the ends of said fixation devices being thickened to have a spherical or lenticular shape or provided with spherical or lenticular elements.

The human circulatory system is comprised of a cardio-vascular circulation and pulmonary circulation. In the embryonic phase of the development of a human being, the two circulatory systems are joined by the ductus arteriosus. The ductus connects the aorta (systemic circulation) with the pulmonary artery (pulmonary circulation). In the normal development of an infant, this ductus closes after birth. In pathological development, the ductus may not close so that the two circulatory systems remain connected even after birth. This can reduce the life expectancy of the infant.

Closure of the ductus by means of a surgical procedure is well-known. However, this procedure is very cost-intensive and is connected with a risk for the patient.

Closure of the ductus by means of an IVALON® (polyvinyl alcohol) foam plug (Porstmann method) is also well-known. In this case, a guide rail is introduced via a femoral vein into the aorta, through the ductus into the pulmonary artery and from there through the right ventricle and the right atrium and finally to the outside again via the opposite femoral vein. The ductus plug is then pushed into the ductus where it is "jammed in place." Owing to the high pressure differential1 between the aorta and pulmonary artery, high demands are placed on the fixation of the ductus plug within the ductus.

For that reason, relatively large plugs must be used which are compressed by about 10 times their length and are 30% larger than the diameter of the ductus. Correspondingly large sheaths are required for introduction of the plug into the femoral artery. In infants, the diameter of the vessels is small and is often not large enough for a procedure of this nature in children weighing less than 30 kg.

In an occlusion device disclosed in DD 233 303 A1, the occluding body has a single-shell, hyperboloid-like basic shape and can be comprised of metal, a metal alloy, plastic and similar materials. Wire-like fixation devices extend outside the occluding body and end in a point so that the risk of injuring vascular walls exists.

In order to implant the occlusion device, it is grasped by a holding wire extending within a safety sleeve and advanced by a catheter. Due to the shape of the occluding body and the pointed ends of the fixation devices, the possibility of withdrawing an improperly implanted occlusion device is associated with considerable danger of injury to the patient.

WO 94/09 706 discloses an occlusion device having a helical basic body from which filaments emanate which evoke clot formation A prosthesis for the closure of an atrial or ventricular septal defect is described in DE 42 22 291 C1. The prosthesis is comprised of a center piece wich is pretensioned via an extension spring from which center piece arms emanate which are in contact with the vascular wall. U.S. Pat. No. 3,874,388 discloses an occlusion device having a basic body from the ends of which fixation devices exercising the effect of an umbrella emanate which can be brought into contact with vascular walls.

In the case of the generic occlusion device according to EP 0 698 373 A2, an injury to the vascular walls by the fixation devices is ruled out. This results in the advantage that a change of position of the occluder itself is readily possible during implantation of the occlusion device. The spherical or lenticular ends of the fixation devices also ensure that if there is a high pressure differential between the vessels joined by the ductus, the fixation elements which are normally in contact with the internal walls of the vessel cannot lead to an injury resulting from movement of the occlusion device. The spherical ends also prevent injury even if the device is possibly transported through the vessels without the protection of a catheter.

SUMMARY OF THE INVENTION

The present invention is an occlusion device of the type named above in which the fixation devices cause no reduction of lumen of the vessels in the walls of which the fixation devices are in contact. It is also to be ensured that the fixation elements do not lead to injury of septa in particular or outer cardiac walls if, for instance, a heart shrinks due to aging. Furthermore, it should be possible to directionally rotate the occlusion device without difficulty in order to bring about an optimum seat.

In accordance with the invention, the fixation device is preshaped and/or pretensioned in such a way that the fixation device is in level contact with the wall surrounding the aperture or follows its direction in the shape of a curve.

In accordance with the invention, the fixation device is preshaped or pretensioned before insertion into a catheter via which the fixation device is introduced to the aperture so that after insertion of the occlusion device, the fixation device or the leg is automatically brought into contact with the wall without perceptibly reducing the lumen of the vessel. The largely level contact with the wall itself produces the advantage of a secure fixation so that the implant does not slip out of place even with large pressure differentials between the vessels or chambers joined by the apertures.

It is particularly provided for that the fixation device is comprised of multiple legs, each of which emanates from the occluding body or the center piece, whereby each leg has a smoothly curved convex shape in relation to the occluding body. Alternatively, there is the possibility that each leg rises radially inward only to slope downwards after reaching a maximum. Other geometrical forms of the wire-like, elastic fixation device are also possible.

As a result of the fact that the fixation device undergoes a specific preshaping, the forces acting on the fixation devices brought about by the passage through the catheter are unable to bring about any such lasting deformation that the fixation devices contact the wall aperture in a non-defined manner.

The fixation devices itself is preferably comprised of shape memory nickel-titanium wires which are given a desired preferred shape by mechanical means and then subjected to heat treatment. In setting the preferred shape, the deformation caused by the passage through the catheter is taken into account.

An occlusion device in which the fixation devices are connected with the center piece extending in the axial direction of the occlusion device, said center piece having a molded part in the form of a connecting piece with an at least partially circumferential groove, in which the molded part can be grasped by guide forceps movable within a catheter during implantation of the fixation devices, is distinguished by the fact that the guide forceps surround the molded part with play at least when being pushed inside the catheter. In particular, the guide forceps engage the groove with play by means of claw-like or hook-like ends.

This measure ensures that the guide forceps with the fixation device can be guided through catheters which are not straight but rather strongly curved. The relative movement between the occlusion device and the guide forceps results in a relatively short rigid unit so that curves of the type mentioned can be passed.

In order to undertake a precise axial rotation of the fixation device so that it can be implanted in the desired positions, a further development of the invention provides for rotation of the fixation device with axial rotation of the guide forceps. For this purpose, a partially circumferential groove may have a cross-section that deviates from a circle, the maximum diameter of which is larger than the maximum inside diameter of the claw-like or hook-like ends of the guide forceps in the position in which the molded part is grasped.

A polyvinyl alcohol foam material is extended and attached to the fixation devices proceeding in or nearly in a plane surface (i.e. a thin sheet of foam). In particular, a polyvinyl alcohol foam such as is commercially available under the trade name IVALON® may be used.

In order to attach the fixation devices in a simple manner, they pass through an opening or a hole drilled in the center piece in which the edges of the opening are deburred or rounded off. This results in an opening which expands conically toward the outside. This ensures that when the thin fixation wires are bent, they are not permanently kinked or even sheared off by sharp edges. However, the particular result is that the fixation wires are in closer proximity to the center piece. As a consequence, catheters of a smaller diameter may be used.

Preferably, the fixation devices extend a spheroid or ellipsoid surface section before insertion into the catheter to ensure that the fixation devices are in linear contact with the vascular wall or cardiac wall to the required degree after implantation, or if a sheet material is extended by the fixation devices, it lies as flat against the wall as possible.

At their outer ends, the fixation devices have atraumatic tips. For example, spherical or lenticular elements may be mounted on the fixation devices which are then pressed, welded or cemented to the outer ends of the fixation devices, making a secure attachment possible. In particular, the spherical or lenticular elements may have a through hole or a blind hole into which the fixation device and a filament can be inserted which are joined to the spherical or lenticular elements by deformation of the spherical or lenticular elements. The edges of the drilled hole or blind holes are deburred or rounded off in order to prevent the fixation device or the filament from being sheared off.

The end of the center piece itself may have a preferably cylindrical attachment having at least one opening for a fixation device. In addition, the head piece may have a larger drilled hole or opening located distally for the attachment of implant of implant material.

The fixation devices, which may also be designed as holding arms, may have grooves either stamped or milled into or on them or elevations with space between them such as rings may be arranged on the fixation devices to be used for the attachment of filaments or implant material.

A further development, provides that the fixation device is bent in the shape of an "S" curve, that at least two S-shaped fixation devices arranged to be offset from each other emanate from at least one end of the center piece, in which the point of intersection of the S-shaped fixation devices may be off center. In particular, the S-shaped fixation devices are peripherally surrounded by a circular envelope in which the center point of the envelope is at a distance from the point of intersection of the S-shaped fixation device is divided into two unequal legs of which each leg has a C-shaped geometry.

These measures ensure that when the occlusion device in accordance with the invention is used to close defects located, for instance, in the vicinity of an outer cardiac wall, injury to the septa caused by the fixation devices does not take place in the event of shrinkage of the heart. For one thing, this is the result of the fact that the free ends of the S-shaped fixation devices are bent particularly in the direction of their intersection at least within the envelopes, so that a bent section of the fixation device is always in contact with the septum. If a septum approaches the vicinity of such a leg, it is only bent in the direction of the occlusion element without the danger of penetration of the vascular wall arising. Alternative shapes such as wires curved in the form of a zigzag which have the function of an axial displacement to avoid injuries to the outer cardiac wall are also possible.

An asymmetrical form or arrangement of the fixation device provides the particular advantage that even apertures located in the vicinity of an outer cardiac wall can be closed without difficulty. In order to be able to properly place the occlusion device, it is of course necessary that the occlusion device can be precisely rotated.

The teaching in accordance with the invention makes it possible to close a congenital defect by conservative measures, i.e., without expensive heart surgery with a heart-lung machine. The procedure is as follows: In order to close an atrial septal defect and patent foramen ovale, a guide catheter is introduced through the femoral vein and the lower vena cava and placed in the right ventricle of a heart.

After passing through the defect in the atrial septum, the distal portion of the implant which may be unfolded in the left atrium in the from of an umbrella (stellate or curved wires as fixation devices with flat foam or similar material extended by them) and drawn back against the septum, precisely due to their own pretensioning. Then the proximal parts of the implant, possibly also an umbrella-like section, independently unfold in the right atrium after removal from the catheter, whereby the system itself is centered in the defect. The insertion forceps are then separated from the center piece or its molded part.

The procedure for closure of a ventricular septal defect is similar in which the installation of a transseptal arterio-venous guide rail may be required for positioning of the insertion sheath (catheter).

Closure of persistent ductus arteriosus takes place in the known manner; however, the occluder may also be in form of an umbrella.

DETAILED DESCRIPTION OF THE PREFERRED EMBODIMENTS

Figure 1:
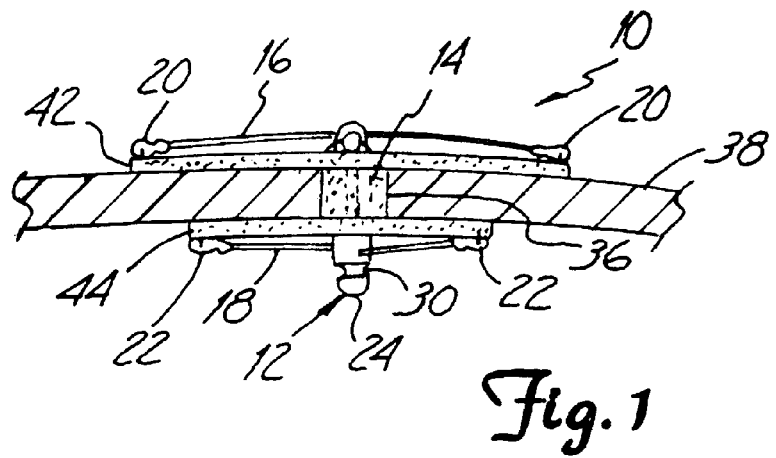
FIG. 1 shows a schematic representation of an occlusion device closing a vascular aperture.
Figure 2:
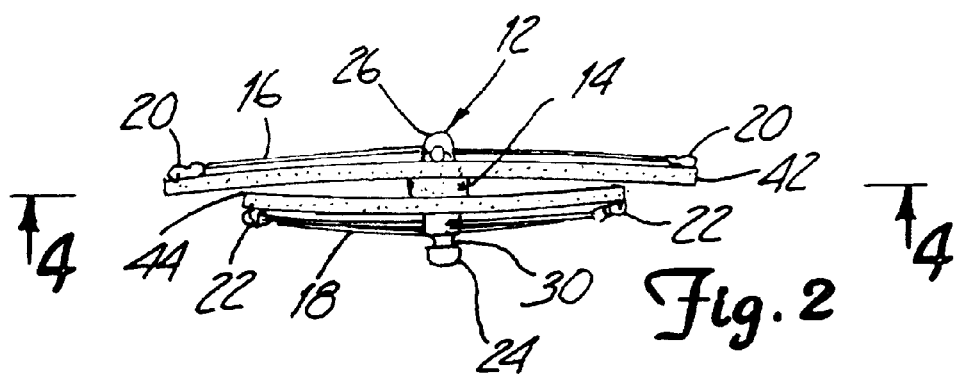
FIG. 2 shows the occlusion device according to FIG. 1 before insertion into a catheter.

In purely schematic form, the drawings show occlusion devices or parts of them intended for the closure of congenital heart defects or vascular apertures such as atrial septal defect, patent foramen ovale, ventricular septal defect or patent ductus arteriosus. As illustrated in FIGS. 1 and 2, from its schematic structure, occlusion device 10 is comprised of a center piece 12, an optional occluding body or plug 14 preferably made from a polyvinyl alcohol (PVA) foam material such as IVALON® surrounding the occluding body as well as wire fixation or holding arms 16, 18 to be designated fixation devices having atraumatic tip elements 20, 22 which assure that holding arms 16, 18 cannot lead to injuries of vascular walls. PVA foam sheets 42 and 44 are attached to arms 16 and 18, respectively.

Figure 11:
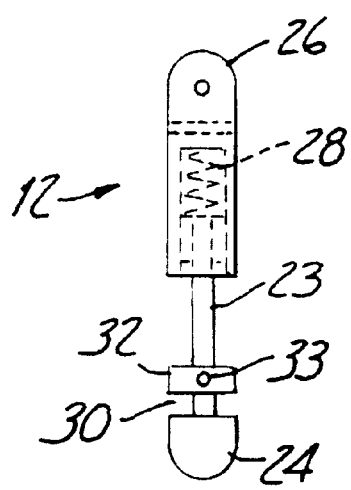
FIG. 11 shows a schematic representation of a center piece of an occlusion device.

Center piece 12 may be made from ceramic, plastic or metals (such as platinum, iridium or titanium) or combinations thereof, and has a bridge-like center section 23 (FIG. 11), a connecting piece 24 as well as a head piece 26. According to FIG. 11, the connecting piece 24 with the bridge-like center section 23 can be telescopically pushed toward the head piece 26 in order to easily adapt to different vessel wall thickness. For this purpose, center section 23 is supported in relation to head piece 26 by means of spring 28. Other well-known adjustment options for varying the length of center piece 12 may also be used, or center piece 12 may be of a fixed length.

Connecting piece 24 adjoins a circumferential groove 30 which, for its part merges into a so-called tail piece 32 having a drilled hole 33 which is rounded off at its edges and can be passed through by holding arms 16, 18 in order to be fixed to tail piece 32 in a simple manner.

A claw-like or hook-like section of insertion forceps, which are not shown, engages connecting piece groove 30. Occlusion device 12 is pushed through catheter 34 to the aperture to be closed with the aid of the insertion forceps. An appropriate insertion device 36 (such as forceps) is shown in purely schematic representation in FIG. 3.

Groove 30 or the geometry of its bottom is designed for the insertion forceps or their sections to engage groove 30 in such a way that relative motion between the two can take place at least in axial direction so that insertion forceps 36 and center piece 12 and thus occlusion device 10 do not appear as a rigid structure. Owing to the relative motion, it is possible for a curved catheter 34 to pass through without difficulty. The structure of center piece 12 and its interaction with forceps 36 is described in greater detail in U.S. Pat. No. 5,702,421 which is hereby incorporated by reference.

Figure 3:
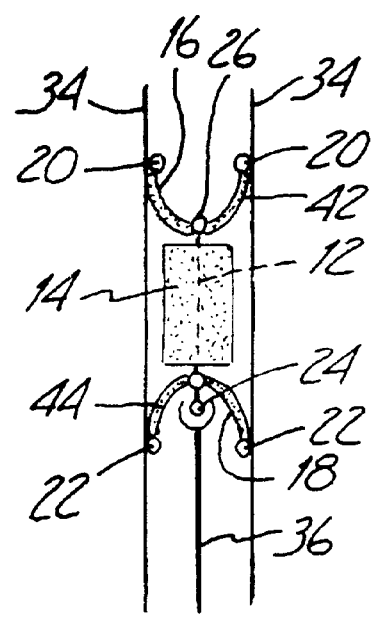
FIG. 3 shows the occlusion device according to FIG. 2 after positioning in a catheter.

As the schematic representation of FIG. 3 illustrates, holding arms 16, 18 are bent toward each other within catheter 34. Due to the small diameter of catheter 34, holding arms 16, 18 undergo a strong deformation which can have an adverse effect in an implanted occlusion device 10 to the effect that the ends of holding arms 16, 18 project away from the vascular wall. This brings about a perceptible reduction of the diameter of the vessel to the effect that there is risk of congestion.

In accordance with the invention, it is provided that the holding arms 16, 18 which may be comprised of nickel-titanium wires are subjected to a precise preshaping before insertion into catheter 34 to the effect that they—as illustrated in FIG. 2—are curved toward each other, thus having a concave shape in relation to plug 14. If holding arms 16, 18, each extending from one end of center piece 12 according to the representation in FIG. 3, are curved toward the center axis and inserted into catheter 34, the deformation caused by this cannot bring about a lasting change in geometry causing the arms to project from the vascular wall when occlusion device 10 is used to close an aperture.

This is illustrated by means of FIG. 1, an aperture 36 in a vascular wall 38 is closed by an occlusion device 10 in accordance with the invention. The center piece 12 with the plug 14 is located within opening 36. Holding arms 16, 18 extend along vascular wall 3 8, the holding arms being in linear or level contact with the outer surfaces of wall 38 so that no reduction of the diameter of the vessel which adjoins vascular wall 38 takes place. As a result of the ends of holding arms 16, 18 being blunted by means of spherical elements 20, 22, there exists no danger of damage to vascular wall 38.

Figure 4:
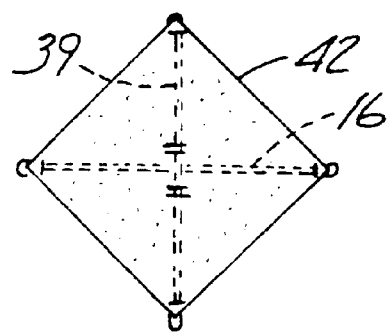
FIG. 4 shows a sectional view of the occlusion device along section 4—4 in FIG. 2.
Figure 5:
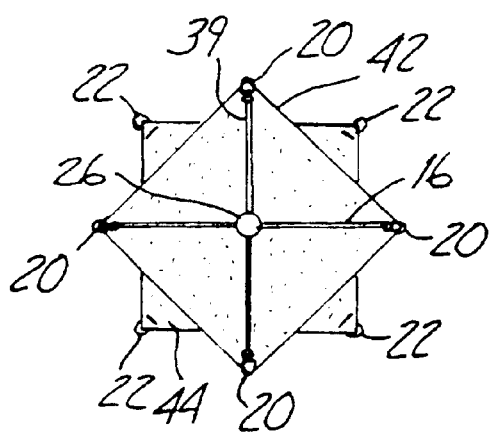
FIGS. 5, 5A and 5B shows a further embodiment of an occlusion device in top plan view, and in top and bottom perspective views.
Figure 6:
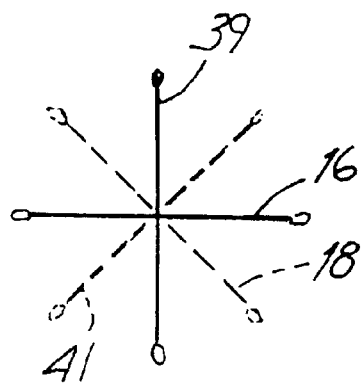
FIG. 6 shows a top plan view of a further embodiment of an occlusion device.

As FIGS. 4 and 5 illustrate, PVA foam sheets 42 and 44 are attached to or carried by holding arms 16, 39 and 18, 41 which emanate from each end of center piece 12. The corresponding foam sheet materials 42, 44 extend a rectangular surface and are sutured, cemented, joined to or molded over holding arms 16, 39 and 18, 41 in another suitable manner. In this connection, rectangular foam sheets 42, 44 are preferably offset in relation to each other and are thus rotated corresponding to the illustrating FIGS. 4 and 5. Accordingly, holding arms 16, 39 and 18, 41 are offset in relation to each other by 45°.

Figure 7:
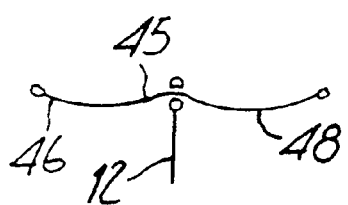
FIGS. 7 and 8 show alternative schematic representations of parts of occlusion devices as seen from the side.
Figure 8:
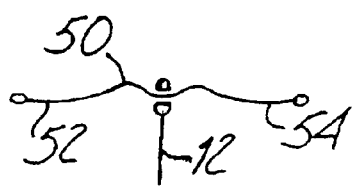
Figure 5A:
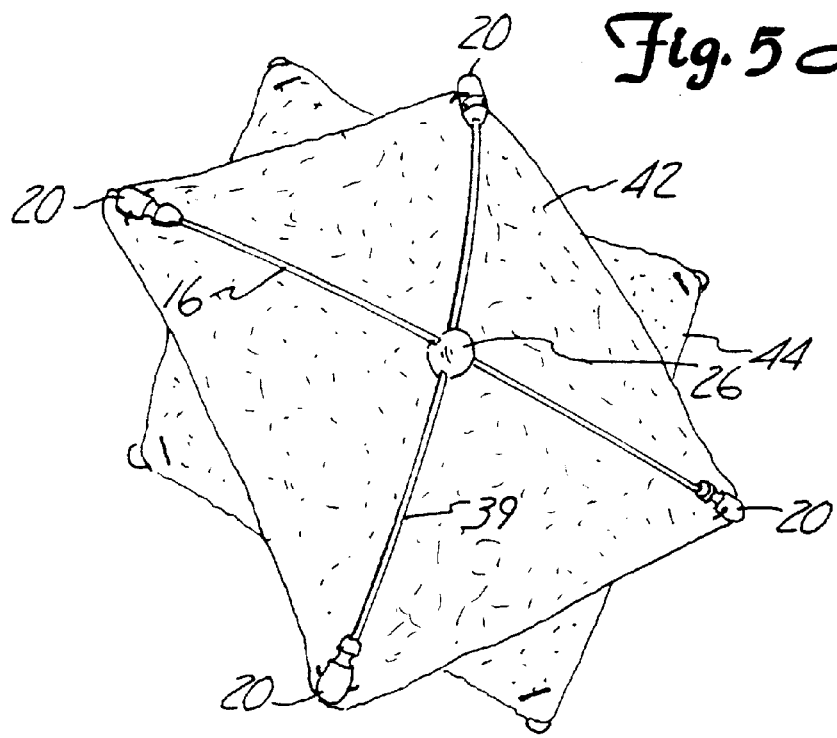
Figure 5B:
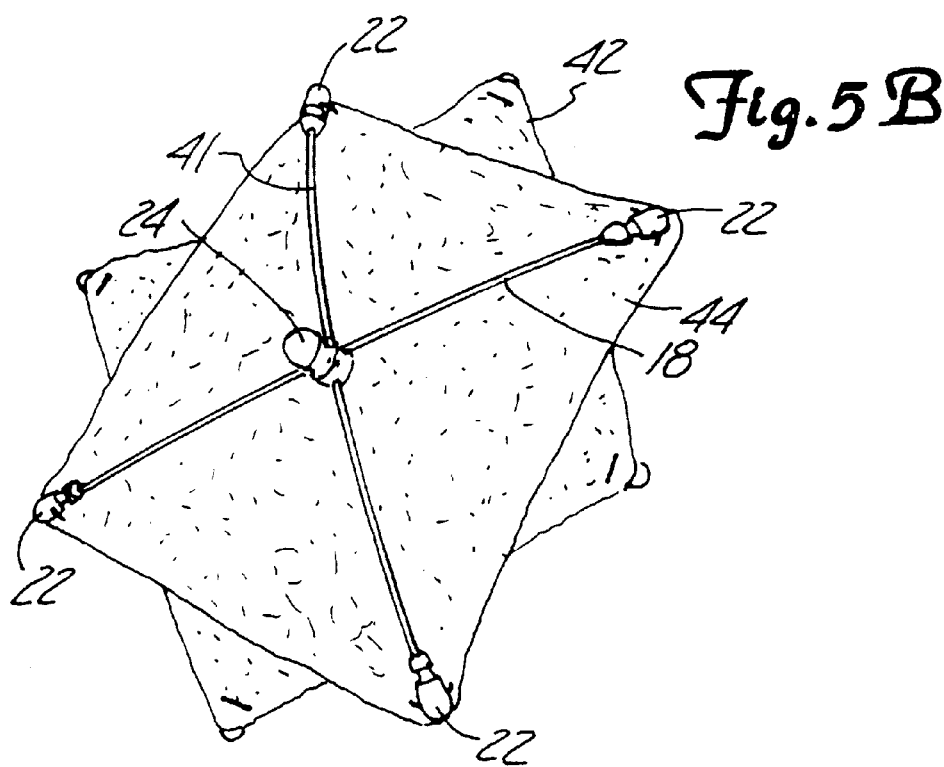

However, holding arms 16, 18 need not necessarily lie flat on vascular wall 38. Rather, other suitable shapes are also possible as illustrated in FIGS. 7 and 8. Thus FIG. 7 shows a holding arm 45 which is comprised of two flat U-shaped legs 46, 48 what emanate from a center piece 12 of an occlusion device. According to FIG. 8, one holding arm 50 is divided into two legs 52, 54, in which each leg rises as it emanates from the center piece only to slope downwards after reaching a maximum. Legs 46, 48 and 52, 54 undergo stress in the direction of center piece 12 during shaping in such a way that the desired contact with vascular wall 38 takes place.

Figure 9:
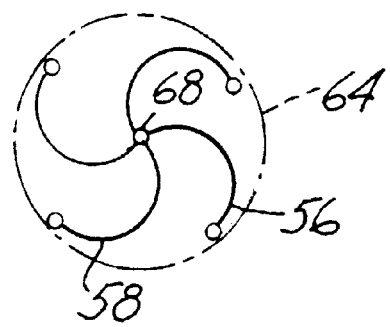
FIGS. 9 and 10 show top plan views of special embodiments of different forms of fixation devices.
Figure 10:
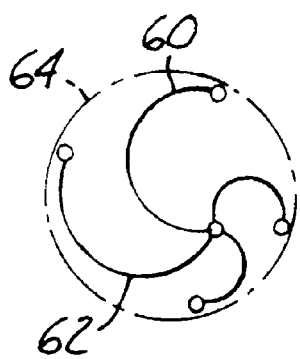

Particularly preferred embodiments arise from FIGS. 9 and 10. Thus holding arms 56, 58 and 60, 62 shaped in the form of an "S" are bent in such a way that they can be enclosed by a circle 64 in the form of an envelope in which the free ends of holding arm 56, 58 and 60, 62 are located within the respective envelope 64. This results in the advantage that in the event of forces acting from the outside on holding arms 56, 58, 60, 62 which, for instance, can occur with the shrinkage of a heart, the free ends cannot lead to injuries of the septa.

If, according to FIG. 9, holding arms 56, 58 are designed to be of equal length emanating from their radially enclosed point of attachment 68, i.e., the point of intersection of holding arms 56, 58 is coincident with the center point of circle 64, then according to the embodiment of FIG. 10, the result is an off-center arrangement of a center point 70, as a result of which holding arms 60, 62 are divided into legs of different length and different curvature. Consequently, the point of intersection of holding arms 60, 62 is not coincident with the center point of circle 64. A corresponding embodiment makes it possible to close a defect located in the vicinity of a septum to a sufficient extent, as the shape of holding arms 60, 62 in relation to the aperture and thus the center piece of the occlusion device is asymmetrical.

In order to precisely inert an occlusion device having holding arms 60, 62 that are asymmetrically shaped with reference to point of intersection or attachment 70, it must be assured that the occlusion device is also rotated within catheter 34 when insertion forceps 36 are rotated. For this purpose, groove 30 must have a proper geometrical shape which ensures that the occlusion device is also rotated when the forceps are rotated.

Figure 13:
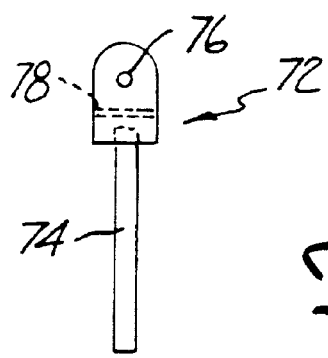
FIG. 13 shows a further embodiment of a center piece of an occlusion device.

As can be seen in FIG. 13, center piece 12 has a head piece 72 having a cylindrical form and which is pressed, cemented or joined by any other suitable means, such as by welding, to a bridge-like center section 74. Head piece 72 may have two openings 76, 78, one of which is used for the passage and attachment of holding arms and the other, preferably distal hole is used for the attachment of implant material (PVA foam sheet).

Figure 12:
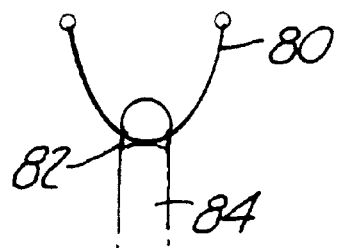
FIG. 12 shows a detail of a center piece of an occlusion device.

In order to ensure that the holding arms and filaments for attachment of implant material passing through holes 76, 78 are not cut of by sharp edges, the outside edges of holes 76, 78 are rounded off as is shown in purely schematic form in FIG. 12. Thus, one holding arm 80 passes through a drilled hole 82 of a center piece 84, in which the outside edges of drilled hole 82 are beveled or rounded off.

Figure 14:
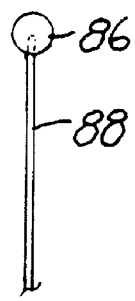
FIG. 14 shows a portion of a fixation device.

The atraumatic tip elements 20, 22 which are mounted on holding arms 16, 18 can be joined with them by pressing, welding or cementing. In FIG. 14, a tip element formed a ball 86 can have a drilled hole into which a holding arm 88 is inserted in order to then press the ball 86.

Figure 15:
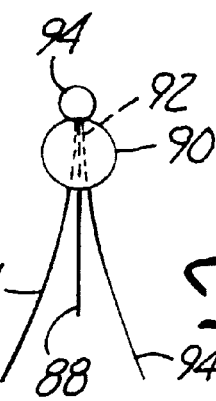
FIG. 15 shows a further embodiment of a fixation device is section.

Corresponding to the illustration of FIG. 15, holding arm 88 passes through a spherical element or ball 90 with a through hole 92. In addition, a filament is passed through the hole which is joined to ball 90 after it is pressed. Filament 94 may then be used for the attachment of PVA foam sheet implant material.

Figure 16:
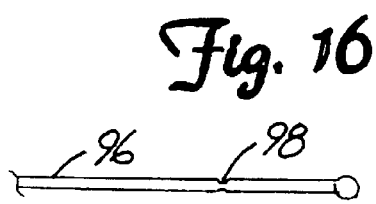
FIGS. 16 and 17 show details of fixation devices.
Figure 17:
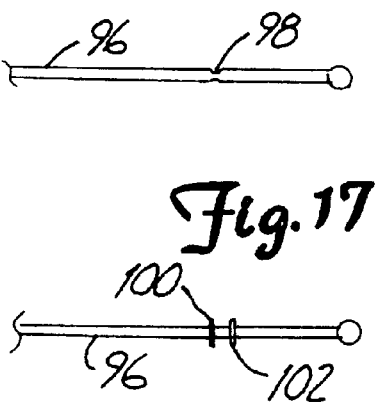

A different fastening possibility is evident from FIGS. 16 and 17. Thus, a groove 98 may be stamped, milled into holding arm 96 as shown in FIG. 16. Alternatively, as shown in FIG. 17, annular thickenings 100, 102 may be attached at intervals to holding arm 96 into or between which the filament can be fixed.

Figure 19:
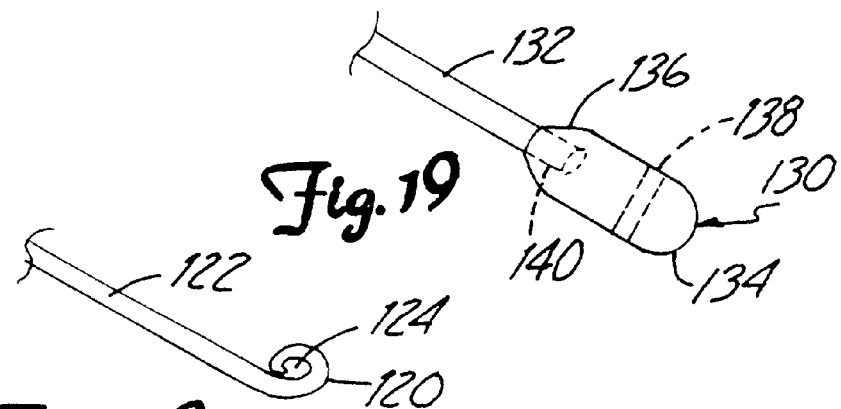
FIGS. 18 and 19 show alternative embodiments of atraumatic tips for the fixation devices.
Figure 18:
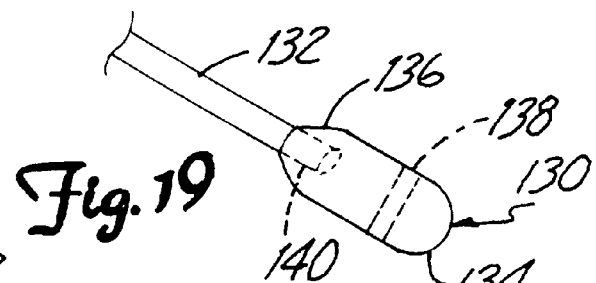

FIGS. 18 and 19 show other embodiments of the atraumatic tip located at the end of each of the flexible wires. In FIG. 18, atraumatic tip 120 is formed at the end of wire 122 by rolling and polishing wire 122 at its distal end. Tip 120 is circular, and includes an aperture 124 through which a filament can extend for suturing the PVA foam sheet to wire 122.

FIG. 19 shows another embodiment in which atraumatic tip 130 is attached to a distal end of wire 132. In this embodiment, tip 130 is a molded, elongated metal body having a rounded distal end 134 and a beveled proximal end 136. Aperture 138 provides the passage for a filament used to suture the PVA foam sheet to tip 130. Blind hole 140 in the proximal end of tip 130 receives the distal end of wire 132.

The atraumatic tip 130 shown in FIG. 19 is particularly advantageous. Its elongated shape makes it easy to crimp tip 130 onto the distal end of 132. The elongated shape makes it easier to drill aperture 138, compared to a similar operation in a spherical-shaped tip.

The beveled proximal end 136 of tip 130 has been found to be particularly important. It provides a smooth surface when pulling the device into a guide cap. With other embodiments of atraumatic tips, a more abrupt junction between the atraumatic tip and the support wire can cause the device to hang up on that junction when the occlusion device is being loaded into the catheter.

It should be mentioned once more that the teaching in accordance with the invention provides the advantage that holding arms 16, 18 are in contact with the vascular walls to the necessary degree and there is no space between them. This is the result of the holding arms, which are extremely deformed when pushed through catheter 34, are pretreated to provide them with the desired geometry so that no lasting deformation takes place when they are bent in the opposite direction which would cause holding arms 16, 18 to jut out when the occlusion device is in position. This preshaping can be achieved by mechanical working and subsequent heat treatment.

Occlusion device 14 and the PVA foam materials 40, 42 extended by holding arms 16, 18 are comprised of a medical-grade polymer in the form of film, foam and/or gel. The attachment to the center piece or to the holding arms may be effected by suturing, cementing or foaming attachment. Preferably, a material is used which is offered under the trade name IVALON®, and is a high density foam.

The thickness of PVA foam sheets 42, 44 when they are dry is between about 0.3 mm and about 4.0 mm. When exposed to blood, PVA foam sheets 42, 44 expand on the order of about 10% in thickness. Preferably, the dry thickness is between about 0.3 mm and about 0.8 mm. PVA foam sheets are preferably formed to these thicknesses by slicing thin sheets of foam from a thicker foam block. A slicing device used for slicing meat to very thin layers is particularly useful in forming PVA foam sheets to the desired thicknesses.

When the PVA foam sheets 42, 44 are generally square, as illustrated in FIGS. 4 and 5, they preferably have diagonal dimensions of between about 5 mm and about 50 mm. In preferred embodiments, diagonal dimensions of between about 18 mm and about 30 mm have been found particularly advantageous.

Center piece or strut 12 preferably has an axial length of about 18 mm or less. In particular, strut 12 preferably has a length of about 2 mm to about 4 mm.

If the holding arms are enclosed by implant material, the particular resulting advantage is that the occlusion device can be securely fixed. However, independent of this, it should be made certain that the dimensions of the implants are selected so that they can be passed through a guide catheter without difficulty and that withdrawal is possible, if the need should arise.

An important advantage of the present invention is that PVA foam sheets 42, 44 immediately block blood flow as soon as they are unfolded during implantation. The physician therefore can test the effectiveness of occlusion device 10 immediately after placement by injecting x-ray contrast fluid through the catheter. If occlusion device 10 is, for any reason, not positioned so that it blocks the aperture, the physician can use the forceps to reposition or remove occlusion device 10. In contrast, prior art devices using DACRON do not initially block blood flow, but rather require clotting to take place in the DACRON over a period of days or weeks. This is known as "residual shunting".

Another important difference is that PVA foam does not rely on clotting as the mechanism for blocking the defect. PVA foam is apparently non-thrombogenic, which reduces the risk of a clot associated with the device breaking loose and causing a stroke.

Another advantage is that PVA foam sheets 42, 44 may be formulated in a radiopaque form, which allows the physician to see the device more clearly during deployment. This enhances proper positioning of device 10.

PVA foam is a proven biocompatible material. The cellular nature of PVA foam promotes rapid endothelialization.

PVA foam sheets 42 and 44 (and optional plug 14) expand considerably when wetted. The softness and expandability allow sheets 42 and 44 (and plug 14) to expand and conform as needed to occlude or fill the defect. This is important because current techniques for determining the size and shape of a defect are not precise.

PVA foam can be shaped in a wide variety of sizes and configurations. It is easily handled and worked in its dry, rigid state, yet is soft and highly compressible after it has been wetted. This permits the fabrication of devices of a wide variety of shapes (both simple and complex). For example, device 10 can be custom formed to fit a particular patient's defect.

Although the present invention has been described with reference to preferred embodiments, workers skilled in the art will recognize that changes may be made in form and detail without departing from the spirit and scope of the invention.

What is claimed is:

1. An occlusion device for the closure of a physical anomaly, the occlusion device comprising:
    a center piece extending in an axial direction;
    upper and lower elongated elastic shape memory fixation devices emanating from the center piece; and
    first and second foldable polyvinyl alcohol foam sheets attached to the upper and lower fixation devices, respectively.

2. The occlusion device of claim 1 wherein the first and second polyvinyl alcohol foam sheets have a thickness of between about 0.3 mm and about 4.0 mm.

3. The occlusion device of claim 2 wherein the first and second polyvinyl alcohol foam sheets have a thickness of between about 0.3 mm and about 0.8 mm.

4. The occlusion device of claim 1 wherein the center piece has an axial length of less than about 18 mm.

5. The occlusion device of claim 4 wherein the center piece has an axial length of about 2 mm to about 4 mm.

6. The occlusion device of claim 1 wherein the fixation devices are preshaped and heat treated nickel-titanium wires.

7. The occlusion device of claim 1 wherein the center piece includes a connecting piece with an at least partially circumferential groove, in which the connecting piece can be grasped by guide forceps movable within a catheter.

8. The occlusion device of claim 1 wherein an atraumatic tip is carried at an outer end of each fixation device.

9. The occlusion device of claim 8 wherein the atraumatic tip has a hole into which a filament can be inserted.

10. The occlusion device of claim 1 wherein the first and second polyvinyl alcohol foam sheets have a diagonal dimension of between about 5 mm and about 50 mm.

11. The occlusion device of claim 10 wherein the first and second polyvinyl alcohol foam sheets have a diagonal dimension of between about 18 mm and about 30 mm.

12. An occlusion device comprising:
    a support structure including a center strut, and first and second flexible arms extending outward from the center strut;
    a first foldable polyvinyl alcohol foam sheet attached to the first flexible arm; and
    a second foldable polyvinyl alcohol foam sheet attached to the second flexible arm.

13. The occlusion device of claim 12 wherein the first and second polyvinyl alcohol foam sheets have a thickness of between about 0.3 mm and about 4.0 mm.

14. The occlusion device of claim 13 wherein the first and second polyvinyl alcohol foam sheets have a thickness of between about 0.3 mm and about 0.8 mm.

15. The occlusion device of claim 12 wherein the center strut has an axial length of less than about 18 mm.

16. The occlusion device of claim 15 wherein the center piece has an axial length of about 2 mm to about 4 mm.

17. The occlusion device of claim 12 wherein the flexible arms are preshaped and heat treated nickel-titanium wires.

18. The occlusion device of claim 12 wherein the center strut includes an at least partially circumferential groove near a proximal end, by which the center strut can be grasped by guide forceps movable within a catheter.

19. The occlusion device of claim 12 wherein an atraumatic tip is carried at an outer end of each fixation device.

20. The occlusion device of claim 19 wherein the atraumatic tip has a hole into which a filament can be inserted.

21. The occlusion device of claim 12 wherein the first and second polyvinyl alcohol foam sheets have a diagonal dimension of between about 5 mm and about 50 mm.

22. The occlusion device of claim 21 wherein the first and second polyvinyl alcohol foam sheets have a diagonal dimension of between about 18 mm and about 30 mm.

23. An occlusion device comprising:
    a center strut;
    a first plurality of elastic fixation devices extending from a first end of the center strut;
    a first foldable sheet of polyvinyl alcohol foam attached to the first plurality of elastic fixation devices;
    a second plurality of elastic fixation devices extending from a second end of the center strut; and
    a second foldable sheet of polyvinyl alcohol foam attached to the second plurality of elastic fixation devices.

24. An occlusion device comprising:
    a center strut having distal and proximal ends;
    a first set of elastic support arms extending from the distal end of the center strut;
    a first foldable sheet of polyvinyl alcohol foam attached to the first set of elastic support arms;

a second set of elastic support arms extending from the proximal end of the center strut; and a second foldable sheet of polyvinyl alcohol foam attached to the second set of elastic support arms.

25. An occlusion device for the closure of a physical anomaly, the occlusion device comprising:

a center piece extending in an axial direction;

first and second collapsible support frames spaced from one another and emanating from the center piece, and first and second foldable polyvinyl alcohol foam sheets attached to the first and second collapsible support frames, respectively.

* * * * *